(12) United States Patent
Soto Peredo

(10) Patent No.: US 8,506,997 B2
(45) Date of Patent: Aug. 13, 2013

(54) PHARMACEUTICAL COMPOUND CONTAINING SILYMARIN AND CARBOPOL, ITS MANUFACTURING PROCESS AND ITS USE AS A REGENERATOR OF THE PANCREATIC TISSUE AND CELLS OF ENDOGENOUS SECRETION DAMAGED BY DIABETES MELLITUS

(75) Inventor: Claudia Angelica Soto Peredo, Mexico City (MX)

(73) Assignee: Universidad Autonoma Metropolitana, Mexico City (MX)

( * ) Notice: Subject to any disclaimer, the term of this patent is extended or adjusted under 35 U.S.C. 154(b) by 844 days.

(21) Appl. No.: 12/453,217

(22) Filed: May 1, 2009

(65) Prior Publication Data

US 2011/0045066 A1    Feb. 24, 2011

Related U.S. Application Data

(63) Continuation-in-part of application No. 10/538,277, filed as application No. PCT/MX03/00108 on Dec. 11, 2003, now abandoned.

(30) Foreign Application Priority Data

Dec. 13, 2002   (MX) .................... PA/a/2002/012315

(51) Int. Cl.
```
A61K 31/357    (2006.01)
A61K 9/48      (2006.01)
A61P 1/18      (2006.01)
A61P 5/48      (2006.01)
```
(52) U.S. Cl.
USPC ........................................ 424/456; 514/452

(58) Field of Classification Search
USPC ........................................ 424/456; 514/452
See application file for complete search history.

(56) References Cited

U.S. PATENT DOCUMENTS

| | | | |
|---|---|---|---|
| 4,844,883 | A | 7/1989 | Patel |
| 2002/0155074 | A1 | 10/2002 | Pinnell |
| 2004/0006128 | A1 | 1/2004 | Bibbs et al. |
| 2004/0157034 | A1 | 8/2004 | Coote et al. |

FOREIGN PATENT DOCUMENTS

JP    2001-261571 A    9/2001

OTHER PUBLICATIONS

Murphy et al., Milk Thistle (*Silybum marianum*), Feb. 16, 2000, The Longwood Herbal Task Force, pp. 1-25.*
Soto et al., Comparative Biochemistry and Physiology, Part C: Pharmacology & Endocrinology, vol. 119c, No. 2, pp. 125-129.
Soto et al., Diabetes & Metabolism, 18th International Diabetes Federation Congress, Paris, France, vol. 29, Aug. 24-29, 2003, p. 4S157.
Schoenfeld et al., CMLS. Cellular and Molecular Life Sciences, Birkhauser Verlag, Basel, CH, vol. 53, No. 11/12, Dec. 1997, pp. 917-920.
Database WPI, Section Ch, Week200205, Derwent Publications Ltd., London, GB; AN 2002-037628.

* cited by examiner

*Primary Examiner* — Jason M Sims
*Assistant Examiner* — Zohreh Vakili
(74) *Attorney, Agent, or Firm* — Birch, Stewart, Kolasch & Birch, LLP.

(57) ABSTRACT

The present invention refers to a new compound containing Silymarin with Carbopol for the treatment of Diabetes Mellitus. This compound morphologically and structurally regenerates the damage that occurs in the pancreatic tissue in Diabetes Mellitus, and regenerates the insulin-producing pancreatic cells (β cells). It therefore regulates the serum levels of this hormone. Furthermore, it restores and maintains the normal concentrations of the blood glucose.

5 Claims, 9 Drawing Sheets
(8 of 9 Drawing Sheet(s) Filed in Color)

PHARMACEUTICAL COMPOUND CONTAINING SILYMARIN AND CARBOPOL, ITS MANUFACTURING PROCESS AND ITS USE AS A REGENERATOR OF THE PANCREATIC TISSUE AND CELLS OF ENDOGENOUS SECRETION DAMAGED BY DIABETES MELLITUS

CROSS-REFERENCE TO RELATED APPLICATIONS

This application is a Continuation-In-Part of co-pending application Ser. No. 10/538,277 filed on Jun. 10, 2005, which is a National Phase of PCT/MX2003/000108 filed on Dec. 11, 2003, which designated the United States, and for which priority is claimed under 35 U.S.C. §120, and under 35 U.S.C. 119(a) to Patent Application No. PA/A/2002/01231 filed in Mexico on Dec. 13, 2002, all of which are hereby expressly incorporated by reference into the present application.

BACKGROUND OF THE INVENTION

Currently, in the pharmacological treatment of Diabetes Mellitus, there is use of insulin and groups of hypoglycemic agents such as the Sulfonylureas, the Biguanides, α-glucosidase inhibitors and Thiazolidinedione derivatives, whose action mechanism works by either stimulating the secretion of insulin or increasing the action of this hormone on the bodily tissues. The half-life of these drugs varies from 1.5 to 48 hours. Although all these drugs, by different action mechanisms, regulate the concentration of blood glucose and/or the secretion of insulin, the duration of their effect is a short period of time and none of them carries out the regeneration of the β-pancreatic cells that produce insulin and that allow the restoration of the function of this hormone. On the other hand, both exogenous insulin and hypoglycemic agents can cause side effects, such as: hypoglycemia, diarrhea, abdominal upsets, nausea and anorexia (Davis, S. and Granner, D., Insulin, Oral Hypoglycemic Agents and the Pharmacology of the Endogenous Pancreas. In: The Pharmacological Basis of Therapeutics. Eds.: Hardman, J. G., Limbird, L. E., Molinoff, P. B., Ruddon, R. W., Goodman, R., $8^{th}$ Ed. pp. 1581-1614, 1996).

None of the medication used currently for the treatment of Diabetes Mellitus regenerates either damaged tissues or cells of endogenous secretion, including the β-pancreatic cells, as the Silymarin and Carbopol compound does. Both in vitro and in vivo, it has been demonstrated that Silymarin has a protective and regenerative activity on the hepatic cells against the damage produced by different toxic substances such as: phalloidin, α-amanitin, alcohol, galactosamine, heavy metals, carbon tetrachloride, toluene, xylene or by certain drugs such as: acetaminophen, indomethacin, isoniazid and tolbutamide (Wellington, K., Harvis, B., Silymarin: A review of its clinical properties in the management of hepatic disorders. Biodrugs. 15: 465-489, 2001) since it has been shown to stabilize the cellular membrane and protect it against free radicals, i.e., it has antioxidative properties by producing an increase in the hepatic glutathione content (free radical scavenger) (Valenzuela, A., Garrido, A. Biochemical basis of the pharmacological action of the flavonoid silymarin and of its structural isomer silibinin. Biol. Res. 27:105-112, 1994).

In humans, Silymarin has been used to treat hepatic diseases such as cirrhosis, poisoning by the fungus Amanita phalloides and exposure to toxic substances (Wellington, K., Harvis, B., Silymarin: A review of its clinical properties in the management of hepatic disorders. Biodrugs. 15: 465-489, 2001).

It has been suggested that free radicals play an important role in the etiology of Diabetes Mellitus, since high serum levels of malondialdehyde (end product of lipoperoxidation) in patients with this disease (Paolisso G, De Amore, A, Di Maro G, D'Onofrio F: Evidence for a relationship between free radicals and insulin action in the elderly. Metabolism, 42:659-66, 1993). Such levels of malondialdehyde are in direct relation to the degree of complications present in patients with Diabetes Mellitus. Defense mechanisms against free radicals include glutathione and antioxidant enzymes such as: superoxide dismutase, glutathione peroxidase and catalase. Soto et al. (Soto C, Pérez B, Favari L, Reyes J: Prevention of alloxan-induced diabetes mellitus in the rat by silymarin. Comp. Biochem. Physiol. 119C:125-129, 1998) reported that Silymarin increases the pancreatic and hepatic glutathione content and therefore its level in blood.

The authors of the aforementioned work also found that Silymarin impeded the elevation of free radicals in the pancreas during the induction of Diabetes Mellitus, which led to a reduction of the blood glucose which is found to be high in this disease.

Taking into consideration the background described, the compound of Silymarin and Carbopol was used as an antidiabetic agent which it is sought to be protected through this application, since it presented an unknown effect as a pancreatic regenerator and controller of the serum concentration of the glucose, which is not regulated in diabetic patients.

SUMMARY OF THE INVENTION

The present invention is drawn to a method of recovering endocrine pancreatic function in a patent in need thereof, by orally administering to the patient an effective amount of a composition comprising silymarin and carbopol, capable of regenerating damaged pancreatic cells.

BRIEF DESCRIPTION OF THE DRAWINGS

This patent or application file contains at least one drawing executed in color. Copies of this patent or patent application publication with color drawing(s) will be provided by the office upon request and payment of the necessary fee.

DESCRIPTION OF THE INVENTION

Figure 1:
FIG. 1 shows the results of treatment Diabetes Mellitus treatment with Alloxan only.

This invention corresponds to the use of Silymarin with Carbopol as a regenerator of the pancreatic tissue and cells of endogenous secretion damaged by Diabetes Mellitus, which suppresses the inconvenient side effects that are presented with the administration of drugs currently used in the treatment of Diabetes Mellitus.

The compound of Silymarin and Carbopol is obtained by the following steps:
  a) Dissolution at 0.5% of Carbopol in deionized water in a magnetic agitator for one hour.
  b) Addition of Silymarin in a percentage of 5 to the foregoing dissolution and subjected to agitation for a minimum period of one hour until a homogenous mixture is obtained.

The homogenous mixture may be presented with any vehicle in formulations for oral administration, such as: solution, suspension, emulsion, hard gelatin capsules, soft gelatin capsules, immediate release tablets, sustained release tablets, prolonged release tablets, controlled release tablets.

An illustrative but not limitative example to demonstrate the pancreatic regenerative activity of the Silymarin and Carbopol compound is found in the one that was administered orally at a dose of 200 mg/Kg, either simultaneously with the diabetogenic agent Alloxan or separately.

The treatment of the Silymarin and Carbopol combined with Alloxan was done in two ways. In the first case, a dose of 200 mg/Kg of the Silymarin and Carbopol compound was administered orally at 6, 24 and 48 hours (two days) after the first dose. In the second case, in addition to the dose mentioned in the first case, the administration was prolonged every 24 hours after the first dose for five more days (seven days). In both cases, the dose of Alloxan was 150 mg/Kg, which was administered subcutaneously one hour after the first dose of the Silymarin and Carbopol compound.

Another example that was also used to demonstrate the pancreatic regenerative activity of the Silymarin and Carbopol compound is in the one that proved the effect of this compound separately with the diabetogenic agent Alloxan, i.e. first the Alloxan was administered and then after 20 days the daily treatment with the Silymarin and Carbopol was begun at the same doses as those already mentioned in the first two cases above, for a period of time from 4 to 7 weeks.

The demonstration of the antidiabetic effect of this Silymarin and Carbopol compound is described in the examples mentioned below.

EXAMPLE 1

Determination of Serum Glucose

The determination of blood glucose was carried out by the Baner method. This consisted in taking 50 µl of serum to which 3.0 ml of ortho-toluidine reagent were added which reacts with aldohexoses and forms glucosamine and a Schiff base, the green color developed has a maximum absorption at 620 nm and is proportional to the quantity of glucose present.

In the case of the combined administration of the Silymarin and Carbopol compound with Alloxan, the determination of serum glucose was done before the administration of the drugs and at 3, 5, 15 and 30 days after the treatment. For the case where the treatment of the Silymarin and Carbopol compound was begun 20 days after the administration of the Alloxan, the determination of the serum glucose was done before the administration of any drug, 20 days after the application of the Alloxan and after each week subsequent to the start of the treatment with the Silymarin and Carbopol compound.

The results showed that in Diabetes Mellitus (treatment with Alloxan only) there was an increase of between 100 and 400% in the serum levels of the glucose compared with the normal values, which range from 80 to 120 mg/dl. The Silymarin and Carbopol compound administered jointly with the diabetogenic agent Alloxan prevented the increase in the concentration of serum glucose that was presented with the administration of Alloxan alone. The results obtained from the treatment with the Silymarin and Carbopol compound started twenty days after the administration of the Alloxan showed that the values of the serum glucose concentration that were significantly high, approximately 400% above the normal value (before starting the treatment with the Silymarin and Carbopol compound) gradually decreased to reach the normal levels in an average time of seven weeks.

The treatment with the Silymarin and Carbopol compound administered alone did not modify the serum glucose concentration.

EXAMPLE 2

Determination of the Concentration of Blood Insulin by the ELISA Method (Enzyme Linked Immuno Sorbent Assay)

This determination was carried out in 10 µl of serum, which was incubated for two hours with monoclonal antibodies aimed against separate antigenic determinants in the insulin molecule. During the incubation, the insulin of the sample reacted with anti-insulin antibodies and with peroxidase-conjugated anti-insulin antibodies. After this time, flushing was done to remove the antibody that failed to combine with the insulin molecules of the sample. 200 µl of 3,3,5,5'-tetramethylbenzidine was then added and the samples remain with this reagent for 30 minutes in order to be able to detect the conjugated compound, which is colored and can be quantified spectrophotometrically. The reaction was finalized by the addition of 50 µl of sulfuric acid and it was read at 450 nm in an ELISA reader in order to be able to determine the insulin concentration in each of the samples.

In the case of the combined administration of the Silymarin and Carbopol compound and Alloxan, the determination of serum insulin was done before the administration of the drugs and at 3, 5, 15 and 30 days after the treatment. For the case where the treatment of the Silymarin and Carbopol compound was begun 20 days after the administration of the Alloxan, the determination of the serum insulin was done before the administration of any drug, 20 days after the application of the Alloxan and at the end of the treatment with the Silymarin and Carbopol compound (when the glucose levels were found to be in the range of the normal values).

The results showed that in Diabetes Mellitus (treatment with Alloxan only) there was a decrease of between 80 and 90% in the serum levels of insulin compared with the normal value, which is 1 ηg/ml. It was observed that the joint treatment of the Silymarin and Carbopol compound and Alloxan impeded the reduction of the insulin serum levels and kept them within the range of the normal value. In the case of the treatment with the Silymarin and Carbopol 20 days after the administration of Alloxan, the insulin serum level was seen to increase to the range of the normal values. These normal values of serum insulin corresponded with those of glucose (example 1).

EXAMPLE 3

Histopathological Analysis of the Pancreatic Tissue

This analysis was done in transversal fragments of pancreas approximately 0.7 cm long corresponding to the head of the organ. Subsequently, by the paraffin embedding technique, 5 µm sections where then obtained, which were stained with the dyes hematoxylin and eosin (HE). This technique consists in: 1) dehydration of the tissue, which is done by passing the tissue through different concentration of alcohol (from 25 to 100%) and then to an alcohol-toluene, toluene-paraffin and paraffin mixture. Once the tissues are dehydrated, blocks are formed with paraffin. 2) Sectioning of the tissue. This is done in a microtome, which is adjusted to the right section thickness of 4 to 6 µm and is placed in a slide. 3) Staining of the sections. This was done with the dyes hematoxylin and eosin.

In the case of the combined administration of the Silymarin and Carbopol compound and Alloxan, the histopathological analysis was done at 3, 5, 15 and 30 days after the treatment. For the case where the treatment of the Silymarin and Carbopol compound was begun 20 days after the administration of the Alloxan, the histopathological analysis was done 20 days after the application of the Alloxan and at the end of the treatment with the Silymarin and Carbopol compound (when the glucose levels were found to be in the range of the normal values, i.e. between 80 and 120 mg/dl).

In Diabetes Mellitus (treatment with Alloxan only) damage occurred in the pancreatic tissue that was observed as cellular disorganization with loss of the islets of Langerhans. Also observed were zones of necrosis, of cellular lysis, hemorrhagic zones, infiltration of lymphocytes, lysis of erythrocytes, as well as an increase in the adipose tissue that forms the capsule of the lobule.

The treatment with the Silymarin and Carbopol compound administered jointly with the Alloxan prevented the tissue damage in the pancreas that occurred in the Diabetes Mellitus, i.e. the tissue presented no alteration. The administration of the Silymarin and Carbopol compound, 20 days after the administration of the Alloxan, regenerated the pancreatic tissue, i.e. all the damage observed in the Diabetes Mellitus was completely reverted and a completely normal tissue was observed.

EXAMPLE 4

Figure 2:
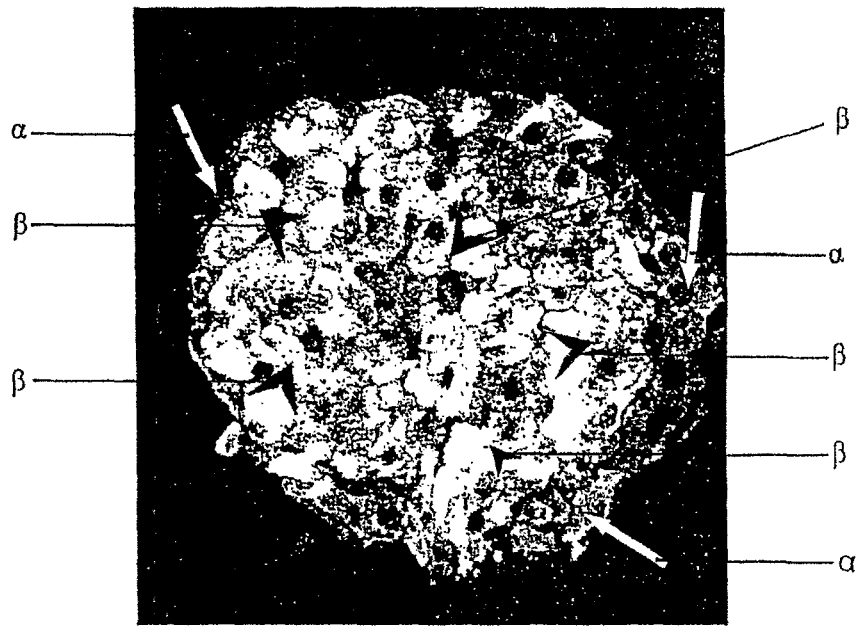
FIG. 2 shows the results of treatment with the Silymarin and Carbopol compound administered jointly with the Alloxan.

Immunohistochemical Analysis for Insulin and Glucagon in the Islets of Langerhans by Confocal Microscopy This analysis is carried out on sections of pancreatic tissue (corresponding to the head of the pancreas). Once the sections have been obtained (described in example 3) they are placed on a slide and the tissue is then deparaffinated and rehydrated. It is begun in pure xylol, with two changes of 10 minutes each. The samples are then passed to a mixture of ethanol-xylol for 10 minutes and afterward to alcohols of different percentages: 100, 90, 80 and 70% for five minutes each. Finally, they are passed to a PBS solution (phosphate buffered solution) for 30 minutes in order to then carry out the immunostaining process. This is begun with the incubation of the samples in a PBS-Triton solution for 10 minutes at an ambient temperature (20-22° C.), they are flushed with PBS without triton and the samples are blocked with albumin in PBS. The samples are flushed with PBS for 1 to 5 minutes. A mixture is then made of primary antibodies anti-insulin and anti-glucagon in PBS and they are left to incubate for approximately 12 hours. At the end of this time, they are flushed with PBS and incubated in a mixture of secondary antibodies coupled with fluorochromes, fluorescein and rhodamine, for one hour at ambient temperature and they are then mounted in a specific medium to preserve the fluorescence. The samples are analyzed by confocal microscopy. In Diabetes Mellitus (treatment with Alloxan only) (FIG. 1) a destruction occurred of the pancreatic islet and only fragments of this were observed with a very scarce presence of insulin (β) y glucagon (α). In the treatment with the Silymarin and Carbopol compound administered jointly with the Alloxan (FIG. 2), the destruction of the pancreatic islet was prevented and this presented an image very similar to that of an islet in normal conditions, i.e. all the cells that form it were shown to be preserved. In most of these, insulin (β) is present, produced from the β cells and only in those of the periphery was the glucagon (α) observed, produced from the α cells.

The administration of the Silymarin and Carbopol compound twenty days after the Alloxan reversed the damage observed in the Diabetes Mellitus, i.e. it caused regeneration of the destroyed pancreatic islet presenting an islet with normal characteristics (described in the previous paragraph), which implies the recovery of the functioning of the β-pancreatic cells and therefore the production of insulin.

This methodology is equivalent to applying it on the human body on any type of Diabetes, since the action level of this composition is at the level of the dysfunction or destruction of the β pancreatic cells and their mechanisms against the cellular damage due to free radicals.

EXAMPLE 5

Determination of the Activity of the Pancreatic Antioxidant Enzymes

A determination was made of the pancreatic activity of the antioxidant enzymes: superoxide dismutase, glutathione peroxidase and catalase. To do such determination, the pancreas was weighed, it was homogenized with a phosphate buffer 50 mM, it was centrifuged at 3000 rpm, and the supernatant was separated. The activities of the aforementioned enzymes was determined in this.

Superoxide dismutase.—This quantification was done by the method of Prasad et al. (1992). Superoxide ions are formed by xanthine and xanthine oxidase. These ions react with the tetrazolium blue and they form a colour compound that can be spectrophotometrically quantified at 560 nm. A unit of superoxide dismutase can inhibit the formation of this compound by 50%.

Glutathione peroxidase.—This quantification was done by the method of Prasad et al. (1992). This enzyme catalyzes the breakdown of $H_2O_2$ by the NADPH. Its activity is measured by the velocity of absorbance change during the conversion of NADPH to $NADP^+$ and this may be spectrophotometrically registered at 300 nm.

Catalase.—This quantification was carried out by the Aebi method (1995). This enzyme catalyzes the breakdown of $H_2O_2$ and the decomposition velocity of the oxygenated water is measured spectrophotometrically at 240 nm.

In the Diabetes Mellitus (treatment with Alloxan only) there was a decrease of between 70 and 75% in the activity of the three enzymes studied: superoxide dismutase, glutathione peroxidase and catalase.

The combined administration of the Silymarin and Carbopol compound and Alloxan showed an increase in the activity of the pancreatic antioxidant enzymes, since this was no different than the control (normal) values.

The administration of the Silymarin and Carbopol compound twenty days after the Alloxan reverted the damage observed in the Diabetes Mellitus in the activity of the three enzymes studied and even values of enzymatic activities higher than normal values were observed (see table).

| Enzymatic activity | Treatment | |
|---|---|---|
| | Alloxan (20 days after its administration) | Silymarin administered 20 days after the application of the Alloxan |
| Glutathione Peroxidase μM NADPH/min/mg prot | 0.016 ± .002 | 0.052 ± 0.002 |
| Superoxide Dismutase U/mg protein. | 4.3 ± 0.02 | 46.5 ± 0.50 |
| Catalase k/sec/mg of protein | 0.01 ± 0.002 | 0.04 ± 0.00 |

EXAMPLE 6

Effects of Silymarin in Rats with Diabetes Mellitus Induced by Alloxan

An analysis of the effects of Silymarin was made with respect to the proliferation of β-pancreatic cells in early stages of a 3-to-21-day Silymarin treatment of rats with Diabetes Mellitus induced by Alloxan.

The methodology included the determination of glucose during treatment. At the end of the treatment, BrdU (5-bromo-2-deoxyuridine) was administered since BrdU is a marker of cells that are being divided. The amount administered was 50 mg/Kg, i.p.

BrdU.—BrdU is used as a proliferation detection technique and acts as a DNA analogue thus substituting the DNA's timidine base and only marking the cells that are being divided.

In the subsequent 18 to 20 hours, the animal was sacrificed. The pancreas was then extracted and put in absorbed formaldehyde in a pH level of 7.0. The tissue was included in paraffin and then 5 μm cuts were made. Immunohistochemical studies were carried out through fluorescence and peroxidase methods to study the proliferation of β-pancreatic cells. The fluorescence painting was observed in a confocal microscope (Zeiss). The cell count was then made with BrdU or insulin marking through the painting with peroxidase in an optical microscope (Zeiss).

The results of the treatment are illustrated in FIGS. 3 through 10.

Figure 3:
FIG. 3 shows the results of a 3-day Silymarin treatment with Alloxan:
  A. The islet of Langerhans with Alloxan treatment for 3 days
  B. The islet of Langerhans with Alloxan and Silymarin treatment for 3 days
  C. Control Sample
  D. The exocrine tissue with Alloxan and Silymarin treatment for 3 days

In FIG. 3, the following is shown in a 3-day Silymarin treatment with Alloxan:
E. The islet of Langerhans with Alloxan treatment for 3 days
F. The islet of Langerhans with Alloxan and Silymarin treatment for 3 days
G. Control Sample
H. The exocrine tissue with Alloxan and Silymarin treatment for 3 days Red marks BrdU with cells proliferating. Green marks insulin with peroxidase with cells producing insulin. Brown marks BrdU-insulin colocation with cells proliferating and producing insulin.

Figure 4:
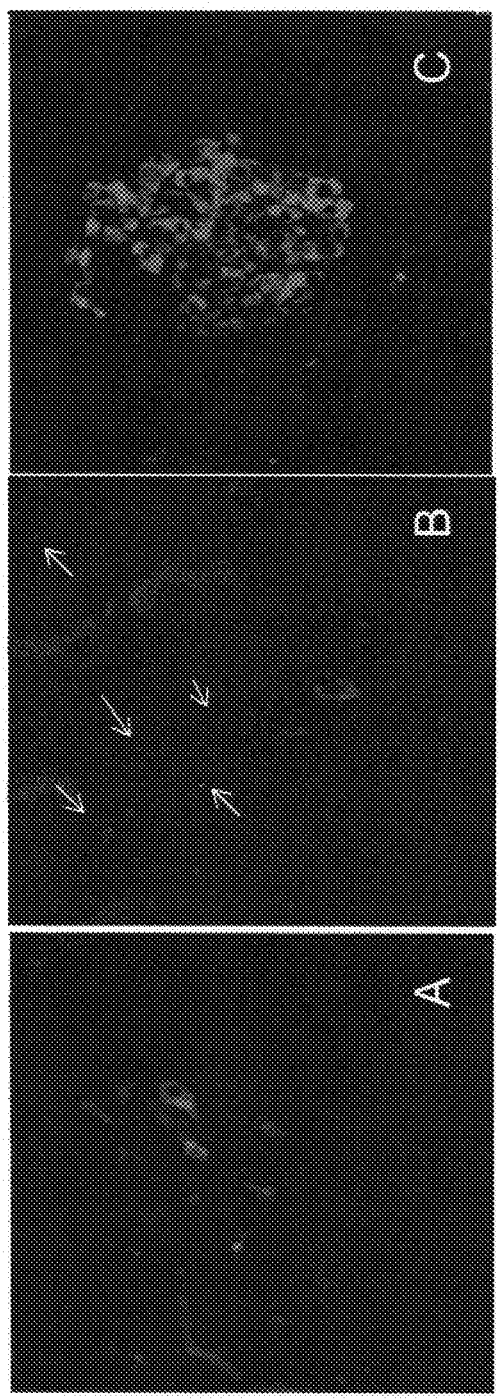
FIG. 4 shows the results of a 7-day Silymarin treatment with Alloxan:
  A. The islet of Langerhans with Alloxan treatment for 7 days
  B. The exocrine tissue with Alloxan and Silymarin treatment for 7 days
  C. Control Sample

In FIG. 4, the following is shown in a 7-day Silymarin treatment with Alloxan:
D. The islet of Langerhans with Alloxan treatment for 7 days
E. The exocrine tissue with Alloxan and Silymarin treatment for 7 days
F. Control Sample Red marks BrdU. Green marks insulin. Brown marks BrdU-insulin collocation.

Figure 5:
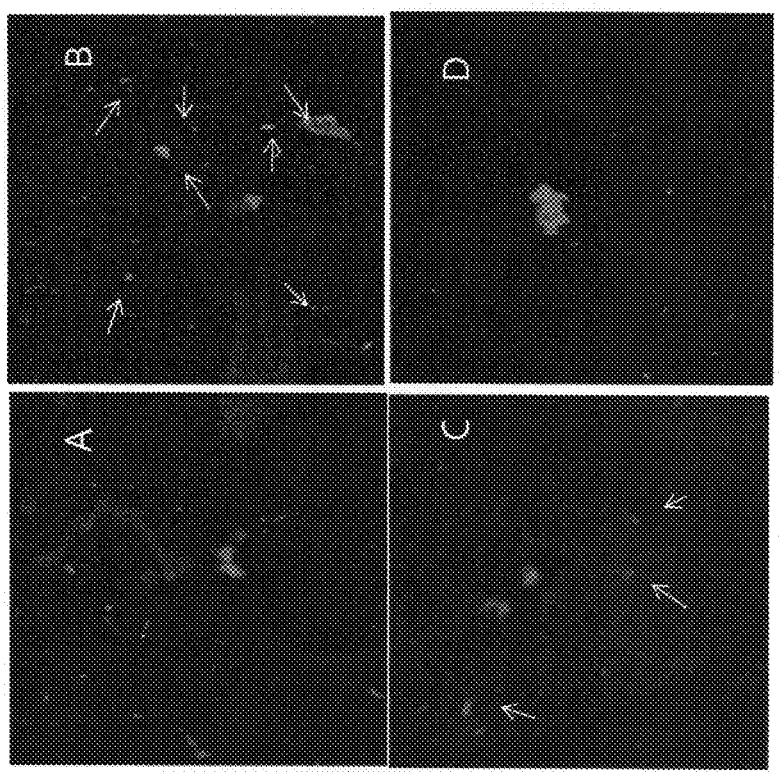
FIG. 5 shows the results of a 14-day Silymarin treatment with Alloxan:
  A. The islet of Langerhans with Alloxan treatment for 14 days
  B. The islet of Langerhans with Alloxan and Silymarin treatment for 14 days
  C. The exocrine tissue with Alloxan and Silymarin treatment for 14 days
  D. Control Sample
Figure 6:
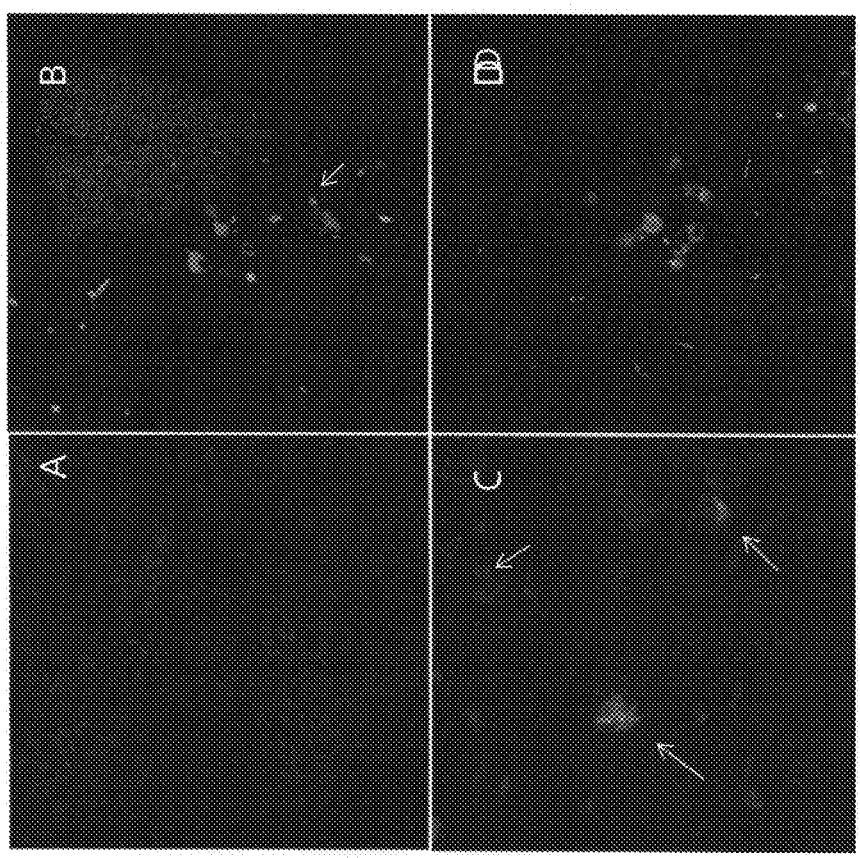
FIG. 6 shows a 21-day Silymarin treatment with Alloxan:
  A. The exocrine tissue with Alloxan treatment for 21 days
  B. The islet of Langerhans with Alloxan and Silymarin treatment for 21 days
  C. The exocrine tissue with Alloxan and Silymarin treatment for 21 days
Figure 7:
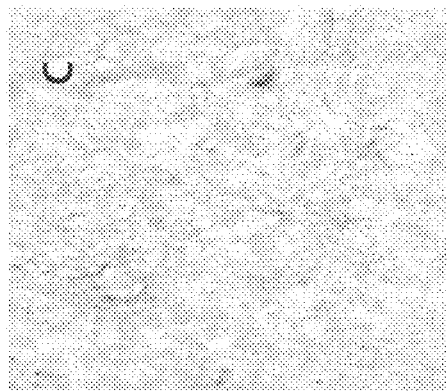
FIG. 7 shows cuts of the pancreatic tissue with Alloxan (insulin) treatment are shown at different times:
  A. 7 days
  B. B. 14 days
  C. 21 days
  D. Control Sample
Figure 7:
Figure 7:
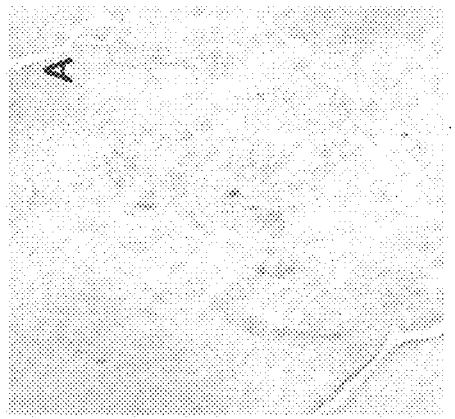
Figure 7:
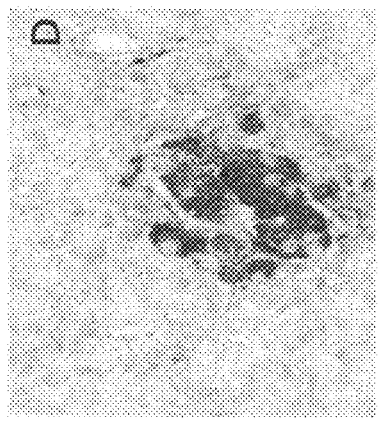
Figure 8:
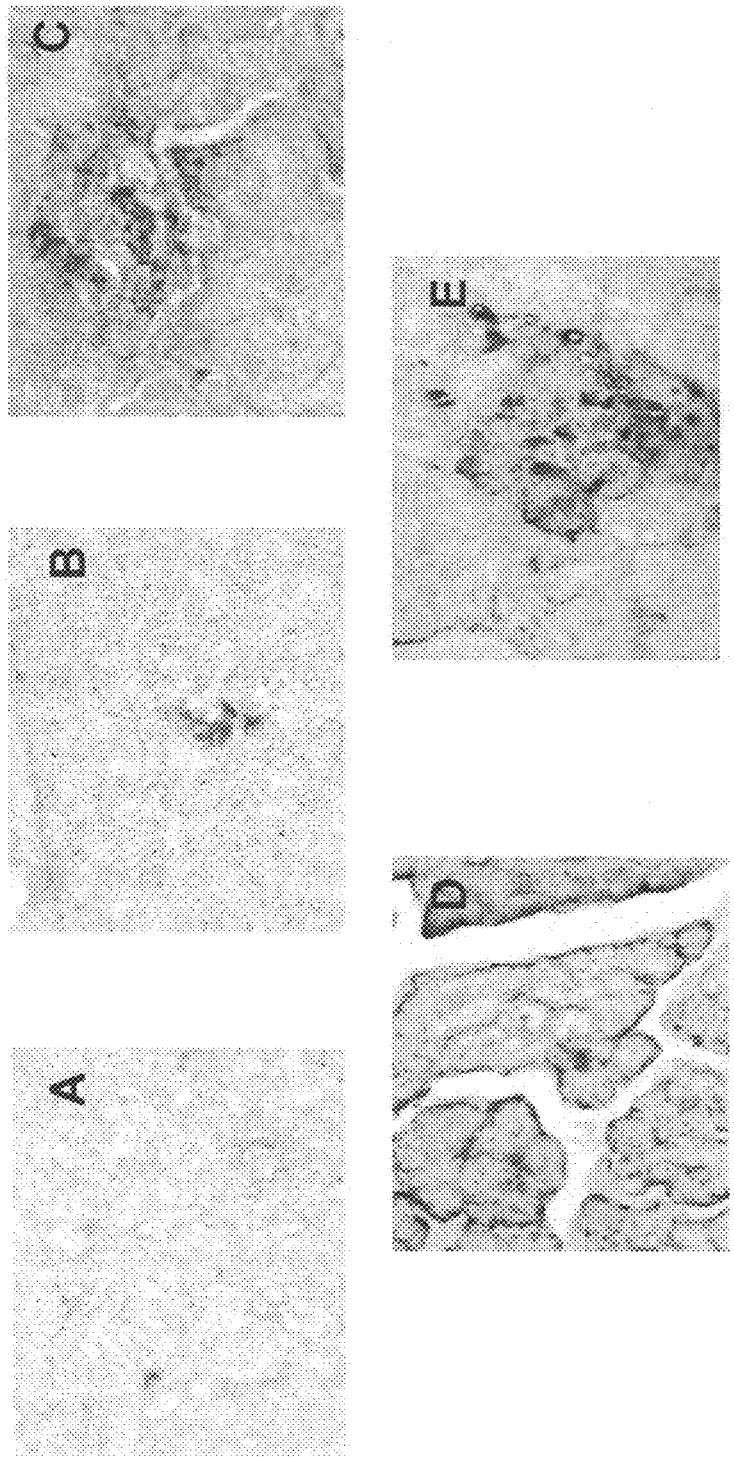
FIG. 8 shows cuts of the pancreatic tissue with Alloxan and Silymarin (insulin) treatment are shown at different times:
  A. 3 days
  B. 7 days
  C. 14 days
  D. 21 days
  E. Control Sample
Figure 9:
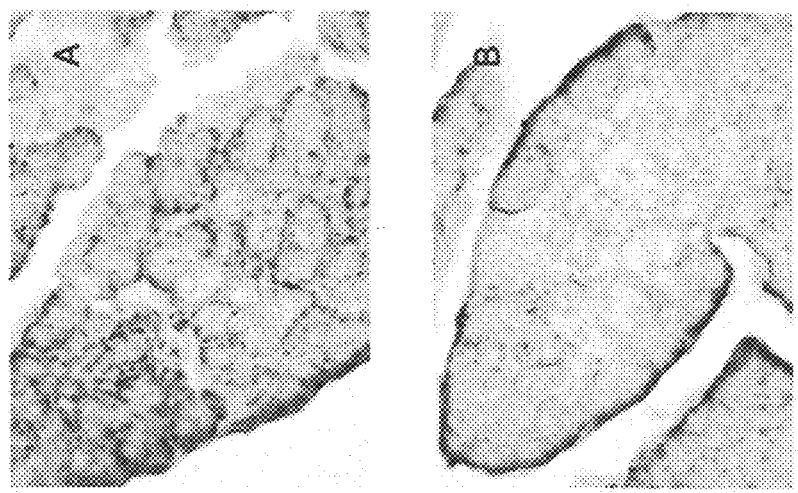
FIG. 9 shows cuts of the pancreatic tissue with Alloxan (BrdU) treatment are shown at different times:
  A. 7 days
  B. B. 14 days
Figure 10:
FIG. 10 shows cuts of the pancreatic tissue with Alloxan and Silymarin (BrdU) treatment are shown at different times:
  A. 7 days
  B. 14 days
  C. 21 days

In FIG. 5, the following is shown in a 14-day Silymarin treatment with Alloxan:
E. The islet of Langerhans with Alloxan treatment for 14 days
F. The islet of Langerhans with Alloxan and Silymarin treatment for 14 days
G. The exocrine tissue with Alloxan and Silymarin treatment for 14 days
H. Control Sample In FIG. 6, the following is shown in a 21-day Silymarin treatment with Alloxan:
D. The exocrine tissue with Alloxan treatment for 21 days
E. The islet of Langerhans with Alloxan and Silymarin treatment for 21 days
F. The exocrine tissue with Alloxan and Silymarin treatment for 21 days In FIG. 7, cuts of the pancreatic tissue with Alloxan (insulin) treatment are shown at different times:
E. 7 days
F. B. 14 days
G. 21 days
H. Control Sample In FIG. 8, cuts of the pancreatic tissue with Alloxan and Silymarin (insulin) treatment are shown at different times:
F. 3 days
G. 7 days
H. 14 days
I. 21 days
J. Control Sample In FIG. 9, cuts of the pancreatic tissue with Alloxan (BrdU) treatment are shown at different times:
C. 7 days
D. B. 14 days In FIG. 10, cuts of the pancreatic tissue with Alloxan and Silymarin (BrdU) treatment are shown at different times:
D. 7 days
E. 14 days
F. 21 days With an analysis of the results outlined above, the effects of Silymarin ascertain the differentiation of the undifferentiated cells of the pancreas and those of intestinal origin.

The invention claimed is:

1. A method of recovering endocrine pancreatic function in a patient in need thereof, which comprises orally administering to the patient an effective amount of a composition comprising silymarin and carbopol, wherein said composition induces the regeneration of damaged pancreatic cells.

2. The method for recovering endocrine pancreatic function according to claim 1, which comprises administering to the patient a composition comprising 3 to 7% silymarin and 0.2 to 0.6% carbopol.

3. The method for recovering endocrine pancreatic function according to claim 2, wherein the composition comprises 5.0% silymarin and 0.5% carbopol.

4. The method for recovering endocrine pancreatic function according to any of claims 1-3, wherein the oral form is a suspension, an oral solution, an emulsion, gel, a hard gelatin capsule, a soft gelatin capsule, an immediate release tablet, a controlled release tablet, a prolonged release or a sustained release tablet.

5. A method of recovering endocrine pancreatic function in a patient in need thereof, which comprises orally administering to the patient an effective amount of a composition comprising silymarin and carbopol for 4 to 7 weeks, thereby regenerating damaged pancreatic cells.

* * * * *